(12) United States Patent
Rahimi

(10) Patent No.: US 10,323,224 B2
(45) Date of Patent: Jun. 18, 2019

(54) VIBRATION DEVICE FOR PETRI DISHES

(71) Applicant: Alireza Rahimi, Ratingen (DE)

(72) Inventor: Alireza Rahimi, Ratingen (DE)

(*) Notice: Subject to any disclaimer, the term of this patent is extended or adjusted under 35 U.S.C. 154(b) by 161 days.

(21) Appl. No.: 15/117,553

(22) PCT Filed: Feb. 6, 2015

(86) PCT No.: PCT/EP2015/052512
§ 371 (c)(1),
(2) Date: Aug. 9, 2016

(87) PCT Pub. No.: WO2015/118106
PCT Pub. Date: Aug. 13, 2015

(65) Prior Publication Data
US 2016/0355775 A1 Dec. 8, 2016

(30) Foreign Application Priority Data
Feb. 10, 2014 (DE) .................. 10 2014 202 372

(51) Int. Cl.
*C12M 1/22* (2006.01)
*C12M 1/42* (2006.01)
(Continued)

(52) U.S. Cl.
CPC ......... *C12M 27/16* (2013.01); *B01F 11/0014* (2013.01); *B01F 11/0031* (2013.01);
(Continued)

(58) Field of Classification Search
CPC ...... C12M 27/16; C12M 23/10; C12M 35/04; B01F 11/0014; B01F 11/0031; B01F 2215/0037
(Continued)

(56) References Cited

U.S. PATENT DOCUMENTS 1,417,219 A * 5/1922 Warren ............... B01F 11/0022
366/212
3,944,188 A * 3/1976 Parker ................. B01F 11/0014
366/110
(Continued)

FOREIGN PATENT DOCUMENTS

AU 2008100675 A4 8/2008
DE 103 02 809 A1 8/2004
(Continued)

OTHER PUBLICATIONS

Isachenko, et al., "Mechanical Agitation During the in vitro Culture of Human Pre-Implantation Embryos Drastically Increases the Pregnancy Rate," Clin. Lab 2010, 56, pp. 569-576.
(Continued)

*Primary Examiner* — Charles Cooley
(74) *Attorney, Agent, or Firm* — Muirhead and Saturnelli, LLC

(57) ABSTRACT

A vibration generator causes a carrier to oscillate, rather than the housing of the vibration generator. The vibration generator is placed within the housing, which itself is not induced to oscillate, thus reducing or eliminating undesired noises due to excessive oscillations of the housing. The vibration generator transfers vibrations to the carrier for Petri dishes using at least one connecting element that is arranged between the carrier and the vibration generator. The connecting element protrudes through the wall of the housing and is sealed by a sealing element with respect to the wall.

25 Claims, 4 Drawing Sheets

(51) Int. Cl.
*C12M 3/06* (2006.01)
*B01F 11/00* (2006.01)

(52) U.S. Cl.
CPC ............ *C12M 23/10* (2013.01); *C12M 35/04* (2013.01); *B01F 2215/0037* (2013.01)

(58) Field of Classification Search
USPC .............. 366/108–128, 208–219; 435/286.7, 435/303.3; 277/398, 503
See application file for complete search history.

(56) References Cited

U.S. PATENT DOCUMENTS

| | | | | |
|---|---|---|---|---|
| 4,054,151 | A | * | 10/1977 | Parker ................. B01F 11/0014 137/110 |
| 4,061,315 | A | * | 12/1977 | Eitzen ................. B01F 11/0014 209/366 |
| 4,202,634 | A | | 5/1980 | Kraft et al. |
| 4,750,845 | A | * | 6/1988 | Nabetani ............. B01F 11/0014 335/219 |
| 5,380,288 | A | * | 1/1995 | Hart ................... A61B 17/3462 277/503 |
| 5,458,343 | A | * | 10/1995 | Dornfeld ................... F16L 5/08 277/503 |
| 6,190,032 | B1 | * | 2/2001 | Choda ................ B01F 11/0014 366/208 |
| 7,311,435 | B2 | | 12/2007 | Heeg et al. |
| 2001/0030906 | A1 | * | 10/2001 | Friedman ............ B01F 11/0008 366/114 |
| 2008/0056059 | A1 | * | 3/2008 | Manera ............... B01F 11/0008 366/110 |
| 2009/0086573 | A1 | * | 4/2009 | Cayley, Sr. ......... B01F 11/0014 366/343 |
| 2010/0330663 | A1 | | 12/2010 | Baumfalk et al. |
| 2016/0355775 | A1 | * | 12/2016 | Rahimi ............... B01F 11/0031 |

FOREIGN PATENT DOCUMENTS

| | | |
|---|---|---|
| DE | 60 2004 011 334 T2 | 1/2009 |
| DE | 10 2008 010 780 B3 | 10/2009 |
| DE | 20 2009 009 980 U1 | 12/2009 |
| DE | 20 2011 101 539 U1 | 9/2011 |
| DE | 10 2012 015 999 A1 | 11/2013 |
| EP | 0 569 214 A2 | 11/1993 |
| EP | 1 284 285 A2 | 2/2003 |
| EP | 1 626 082 B1 | 1/2008 |
| EP | 2 419 503 B1 | 12/2012 |
| JP | 63007829 A * | 1/1988 |
| JP | S 64-58335 A | 3/1989 |
| JP | 2004255222 A * | 9/2004 |
| KR | 10 2003-0013354 A | 2/2003 |
| WO | WO 96/28243 | 9/1996 |
| WO | WO 98/32838 | 7/1998 |
| WO | WO-9832838 A1 * 7/1998 .......... B01F 11/0008 |  |
| WO | WO 2010/118709 A2 | 10/2010 |

OTHER PUBLICATIONS

Isachenko, et al., "In-vitro culture of human embryos with mechanical micro-vibration increases implantation rates," Reproductive BioMedicine Online, Jun. 2011, 22, pp. 536-544.

Isachenko, et al., "Cryopreservation of human ovarian tissue by direct plunging into liquid nitrogen," Cryo Letters, Sep.-Oct. 2002, 23/5, pp. 333-344, Abstract Only.

* cited by examiner

VIBRATION DEVICE FOR PETRI DISHES

TECHNICAL FIELD

The system described herein relates to a vibration device, and more particularly to a vibration device for Petri dishes.

BACKGROUND

Such vibration devices are, for example, known from DE 10 2012 015 999 A1. Here, the vibration body is the housing of the device itself. The device described therein is, for example, used in the in vitro fertilization and maturation of live egg cells, more particularly human egg cells. The medical background for mechanical agitation in in vitro fertilization is explained in the article "Mechanical Agitation During the in vitro Culture of Human Pre-Implantation Embryos Drastically Increases the Pregnancy Rate", Clin. Lab. 11+12/2010, pages 569-576. For good chances of success, the vibration devices are used to generate oscillation frequencies of below 40 Hz, with quite small oscillation amplitudes of usually less than 1 mm, for example 0.2 mm.

The oscillation frequency and the oscillation amplitude can act on the embryo cultures with variation over time. In particular, the oscillation frequency changes over time to the effect that it, for example, increases steadily from 5 Hz to 20 Hz. With known devices, it is possible to achieve quite good results. However, a homogeneous agitation of all cultures arranged on the known devices was not always guaranteed. Also, the service life of the known devices was not always satisfactory and it was frequently not possible to achieve reliable operation with constant vibration parameters over a relatively long period of a few weeks or months.

Other devices for the mechanical agitation of cell lines are, for example, revealed by the document EP 2 419 503 B1. Here, a cell line in a culture medium in a culture flask is exposed to a vibration. The culture flask is fastened on a mobile platform mounted on a stationary carrier via spring elements.

Yet further agitation devices are known from U.S. Pat. No. 4,202,634 A, EP 0 569 214 A2 and DE 103 02 809 A1.

It is desirable to increase the long-term reliability and durability of a vibration device.

SUMMARY OF THE INVENTION

This system described herein provides a vibration generator that is connected to the carrier via at least one connecting element protruding through a wall of the housing, and a sealing element seals the connecting element with respect to the wall of the housing.

In other words, the vibration generator causes a carrier, rather than the housing itself, to oscillate. In this connection, the vibration generator is placed within the housing, which itself is not induced to oscillate. Undesired noises due to excessive oscillations of the housing consequently fail to materialize. So that the vibration generator can transfer the vibrations to the carrier for the Petri dishes, at least one connecting element is arranged between the carrier and the vibration generator. The connecting element protrudes through the wall of the housing and is sealed by a sealing element with respect to said wall.

Consequently, all oscillating parts except for the carrier and a segment of the connecting elements are situated within the housing. The housing wall itself is not induced to oscillate or is induced to oscillate only to a minimal extent. Only the carrier arranged above the housing is induced to oscillate by preferably three to four connecting elements. In this case, the penetration of the connecting elements through the cover wall of the housing is sealed by sealing elements. This ensures that, within the region of the penetration of the connecting elements, no sound reaches the outside and no water enters the housing. This has considerable effects on the service life of the vibration device. The vibration device is used in very humid and warm incubators. Incubators generally have an air humidity of close to 100% and a temperature of close to 40° C. The treatment of the fertilized egg cells extends over several hours or even days. The vibration device usually stays in the incubator over several treatment cycles. During opening of the door of the incubator, in the event of a temperature drop in the incubator or during removal, the vibration device cools down. The seal between the connecting element and the wall of the housing prevents the warm and humid air in the incubator from entering the housing of the vibration device and prevents corrosion damage possibly arising as a result.

In practice, the vibration generator can be fastened to a vibration body and the connecting element itself can likewise be fastened on the vibration body. The vibration body has a predefined mass which is induced to the optimal oscillation frequency and oscillation amplitude by the vibration generator. In the case of a relatively high dead weight of the vibration body, the influence of the low mass of the Petri dishes and their content on the vibrations generated is negligible. The vibration body too is situated within the housing, and so the vibration body too does not induce any structural elements or air molecules to vibrate outside the housing. In practice, vibration bodies and connecting elements can consist of hard and rigid material such as metal or hard plastic. The oscillations of the vibration body that are caused by the vibration generator are, owing to the hard and rigid material of the vibration body and of the connecting elements, completely transferred to the carrier, which preferably likewise consists of hard and rigid material. This ensures that the same vibration conditions (amplitude, frequency) prevail at each spot of the carrier.

In practice, the vibration body can be supported on a foot. The foot can either likewise be arranged within the housing on its base or form the base element of the housing itself. The vibration body is held in a movable manner in relation to said foot. More particularly, the vibration body is held in a movable manner in a horizontal plane by means of the foot. For this purpose, either a low-friction supporting element or a spring element can be arranged between the vibration body and the foot.

The vibration body can be supported on the foot via a low-friction area, for example the surface of an element composed of polytetrafluoroethylene (PTFE), a low-friction plastic. The vibration generator is fastened firmly to the vibration body and causes it to oscillate in a horizontal plane. A low-friction supporting area, such as, for example, a supporting element composed of PTFE, can reduce the friction between vibration body and foot and make the movement of the vibration body smooth.

Alternatively, a spring element is arranged between vibration body and foot. The spring element can have a resonance frequency within the region of the desired vibration frequency. In this case, a very high operating time of the vibration device can be realized with an only slight vibration energy.

Furthermore, it is possible to arrange in the wall of the housing a pressure equalization element which allows gas molecules to pass through and holds back liquid molecules. Such pressure equalization elements are known for housings of electronic instruments. For example, they are provided by Bopla Gehäuse Systeme GmbH in 32257 Bünde or by W.L. Gore & Associates, Inc. in Newark, Del., USA and are designed to comply with different testing standards, for example IP64, IP65, IP67, IP68 or IP69. Such pressure equalization elements, known as vents, allow, as said, air molecules or other gas molecules to pass through, but hold back liquid molecules and dust molecules. This keeps the interior of the housing free of contaminants and, in particular, of liquid. Specifically because of the location of the vibration device within an incubator at high temperature and air humidity, there is the risk of condensation moisture penetrating into the housing. The vibration device cools down when the temperature drops in the incubator or the door is opened or when operation of the incubator is interrupted. The gas volume within the housing of the vibration device contracts during cool-down and sucks in air from the outside. Water molecules entering with the air would condense in the housing and lead to corrosion and soiling of the structural elements within the housing. Water molecules are held back by the pressure equalization element.

Furthermore, it is possible in practice for the carrier for the Petri dishes to be formed by a plate having indentations, the diameter of which corresponds in each case to the diameter of a Petri dish. The Petri dishes can thus be simply placed onto the plate of the vibration device. This involves the base of the Petri dish entering an indentation, and so the Petri dish is immovably fixed on the carrier in a horizontal direction. The vibrations of the carrier in a horizontal plane are consequently transferred to the Petri dishes held in the indentations.

In practice, there can be provision for three or four connecting elements. The connecting elements are preferably connected to the carrier by means of a fastening screw. For this purpose, the connecting element can have an internal thread into which the external thread of the fastening screw is screwed.

According to the already known prior art, the vibration device is an electric motor having an imbalance on the motor axis. In addition to the elements described so far, an electronic control system for controlling the operation of the electric motor can be arranged in the housing. In the electronic control system, it is possible by means of a keyboard or by means of a digital data interface to predefine certain operating programs, which predefines the duration of operation of the electric motor and possibly the speed of rotation of the electric motor, which determines the vibration frequency.

In practice, there can be provision for a limitation means for the amplitude of the vibration. Such a limitation means avoids unallowably high amplitudes, which can have an adverse effect on the successful fertilization and maturation of the fertilized egg cell. Furthermore, an option to adjust the limitation means can make it possible to alter the maximum amplitude, and so different values for the maximum amplitude can be set.

BRIEF DESCRIPTION OF DRAWINGS

Embodiments of the system described herein will be described below with reference to the accompanying drawings.

DETAILED DESCRIPTION OF VARIOUS EMBODIMENTS

Figure 1:
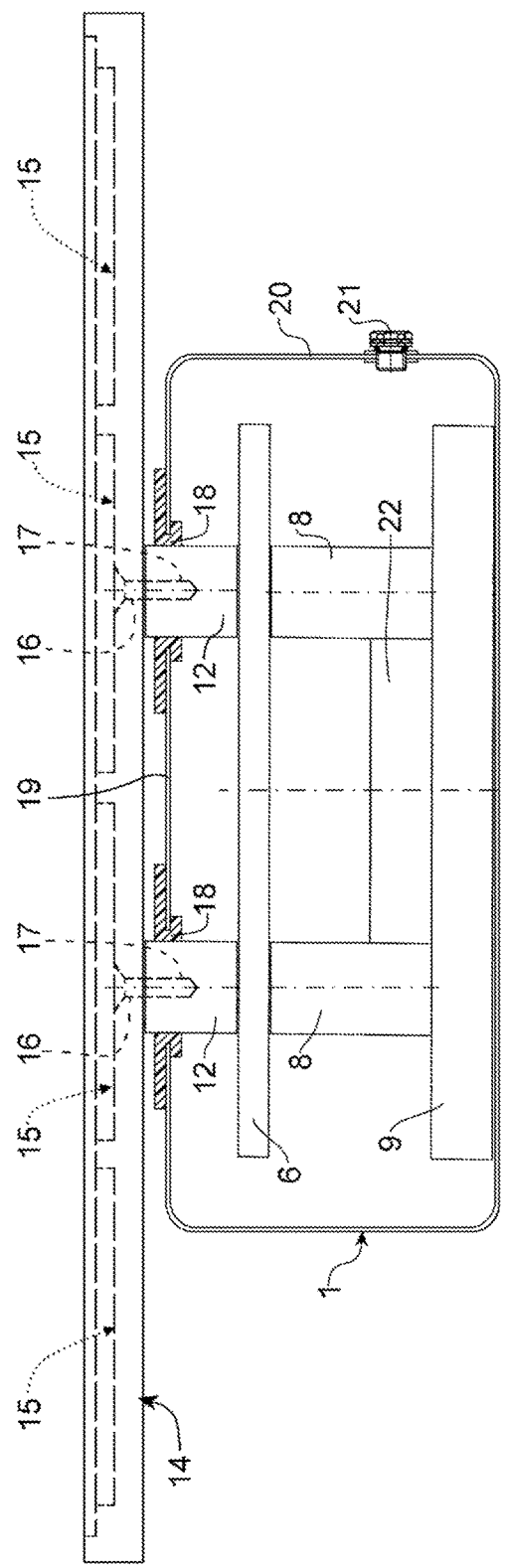
FIG. 1 shows a schematic representation of a side view of a vibration device having a cut housing.
Figure 2:
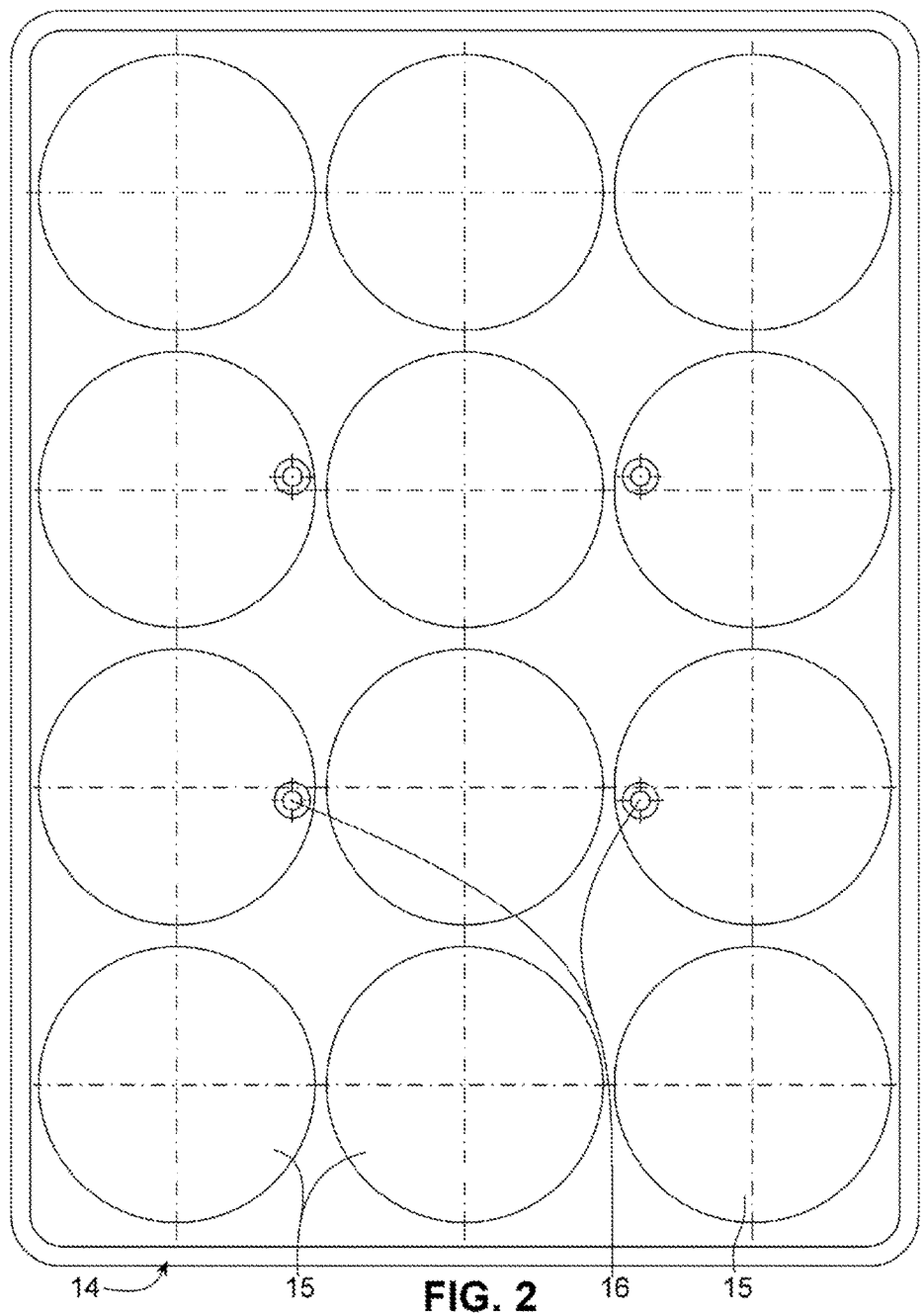
FIG. 2 shows a top view of the vibration device from FIG. 1.
Figure 3:
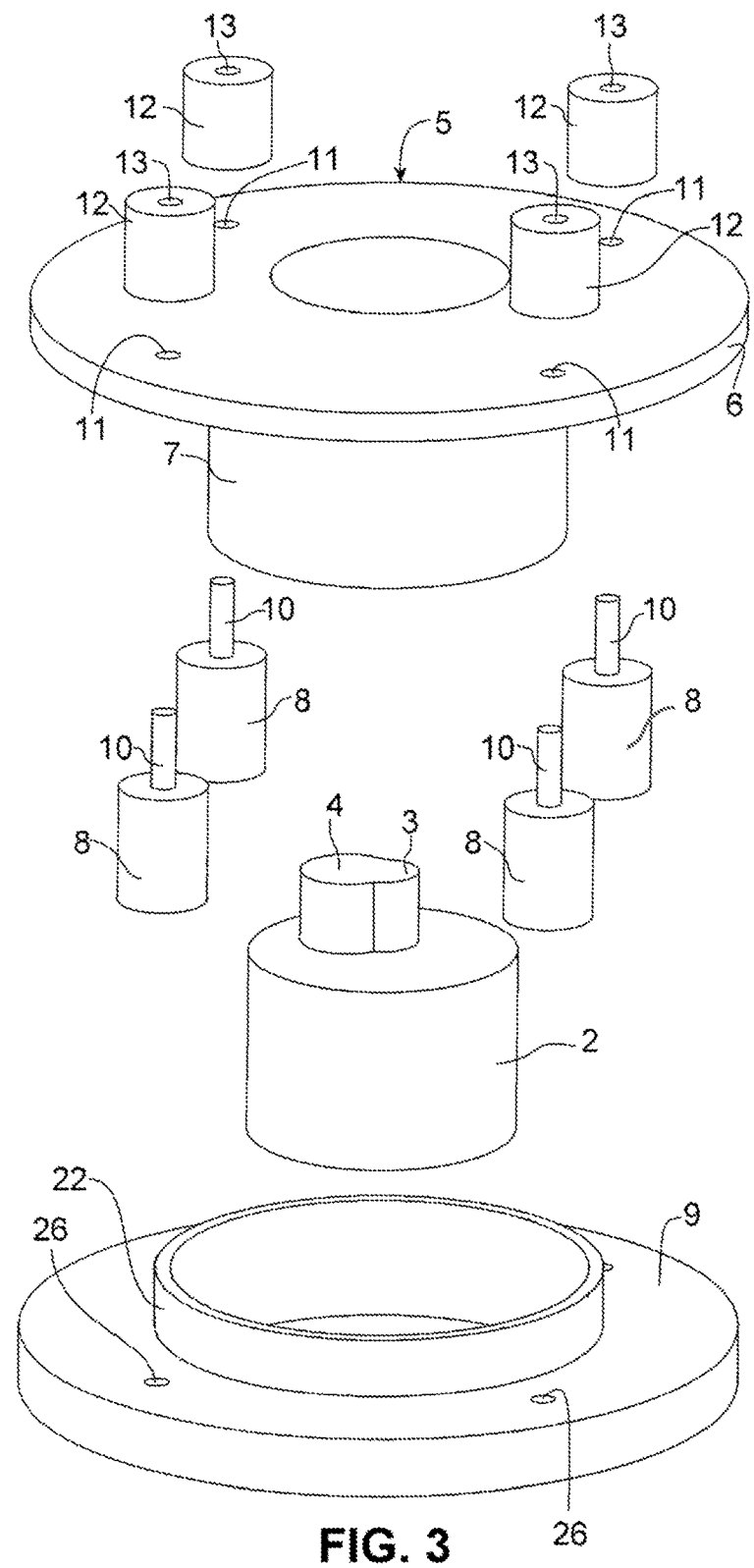
FIG. 3 shows a three-dimensional exploded view of the structural elements of the vibration device from FIGS. 1 and 2, said elements being arranged in the housing.

The vibration device from FIGS. 1 to 3 comprises a housing 1, which is shown schematically in FIG. 1 as a simple sheet housing. It is self-evident that a plastics housing and any other housing type is alternatively suitable for the production of the herein described vibration device.

Arranged in the housing 1 is a vibration generator 2, which is shown schematically in FIG. 3. The vibration generator 2 is an electric motor, on the motor axis 3 of which an imbalance 4 is fastened. The motor axis 3 is oriented perpendicularly, and so, during rotation of the motor axis 3 of the electric motor 2, the imbalance 4 generates a centrifugal force directed outwards in the direction of the imbalance 4. The electric motor 2 is firmly arranged within a vibration body 5, which consists of a circular-disk-shaped flange plate 6 and a cylinder-barrel-shaped accommodation segment 7, into which the vibration generator 2 is inserted. The vibration body 5 is connected to a foot 9 via rubber elastic spring elements 8. For this purpose, the foot 9 has screw holes 26, through which fastening screws (not shown) protrude. The external threads of the fastening screws are screwed into the internal thread on the bottom side of the spring elements 8. Fastened to the top side of the spring elements 8 are threaded bolts 10 which are inserted through through holes 11 in the flange plate 6 and are screwed into the internal thread 13 of connecting elements 12. The connecting elements 12 consist of hard plastic or light metal or some other rigid material, and so they transfer movements of the vibration body 5 directly to a carrier 14 (see FIG. 1).

The carrier 14 is formed by a plate, composed of plastic or light metal for example, which has multiple indentations 15. Each indentation 15 has a diameter of 55 mm, corresponding to the customary diameter of Petri dishes. Particularly in FIG. 2, it can be seen that such a plate 14 can have, for example, twelve indentations for accommodating Petri dishes. Four screw holes 16 are arranged in the middle region of the plate 12. Protruding through them are fastening screws 17, by means of which the plate 14 is screwed tight to the connecting elements 12.

It can be further seen in FIG. 1 that, in each case, one sealing element 18 seals one connecting element 12 with respect to one penetration opening in the upper wall 19 of the housing 1. The diameter of the penetration opening for the connecting elements 12 is larger than the diameter of the connecting elements 12 themselves by several millimeters. The penetration opening itself is filled with a very soft silicone seal which forms the sealing element 18. The silicone seal 18 consists of a soft rubber-type material which, during processing, adheres firmly to the surface of the connecting element and of the upper wall 19 of the housing 1. After setting, the free surface of the silicone seal 18 loses its adhesive property, but continues to firmly stick to the surfaces of the upper wall 19 of the housing 1 and of the connecting elements 12 that were wetted during processing. Contact between the sealing element 18 and the adjacent surfaces is gas-tight. Since a very soft silicone is used to form the sealing element 18, the sealing elements 18 do not generate any relevant resistance to the relative movement of the connecting elements 12 in relation to the upper wall 19 of the housing 1. In practice, the use of a silicone gel from WACKER Chemie AG, Munich has become established for the production of the sealing elements 18, which gel is sold under the name SilGel® 612 A/B. SilGel® 612 A/B is a pourable, room-temperature-vulcanizable addition-curing two-component silicone rubber which does not vulcanize to give a conventional silicone rubber, but yields a soft, gel-type vulcanizate.

This construction ensures that all structural elements induced by the vibration generator (electric motor 2) are substantially situated within the housing 1. By means of the housing 1, sound generated by the elements induced to vibrate is largely absorbed. The corresponding vibration device is consequently largely silent.

Furthermore, this sealing prevents liquid from entering the housing 1 in the region of the connecting elements 12. As explained above, the vibration device is preferably used in incubators, in which a high air humidity and a high temperature prevail. The measure of sealing the interior of the housing with respect to moisture considerably increases the service life of the electronic structural elements within the housing 1.

A pressure equalization element 21 is screwed into a side wall 20 of the housing 1. Such pressure equalization elements are used in the production of housings of electronic instruments in order to allow the housings to be ventilated without entry of water. The pressure equalization element 21 allows gas molecules to pass through, but prevents liquid molecules from entering or leaving.

Pressure equalization in the housing 1 is necessary because the vibration device is used in incubators, in which a temperature of up to 40° C. prevails. During lowering of the temperature in the incubator or during removal of the vibration device, said device can cool down to room temperature from 15° C. to 20° C. The gas within the vibration device, said gas expanding upon warming and contracting upon cooling down, can enter and leave through the pressure equalization element 21.

The lower region of the accommodation segment 7, as can be seen in FIG. 3, can project into a ring 22 which is formed on the upper side of the foot 9. In this case, the ring 22 can surround the accommodation segment 7 of the vibration body 5 with a slight play of less than 1 mm.

The slight play limits the amplitude of the vibration movement of the vibration body 5 with respect to the foot 9.

Figure 4:
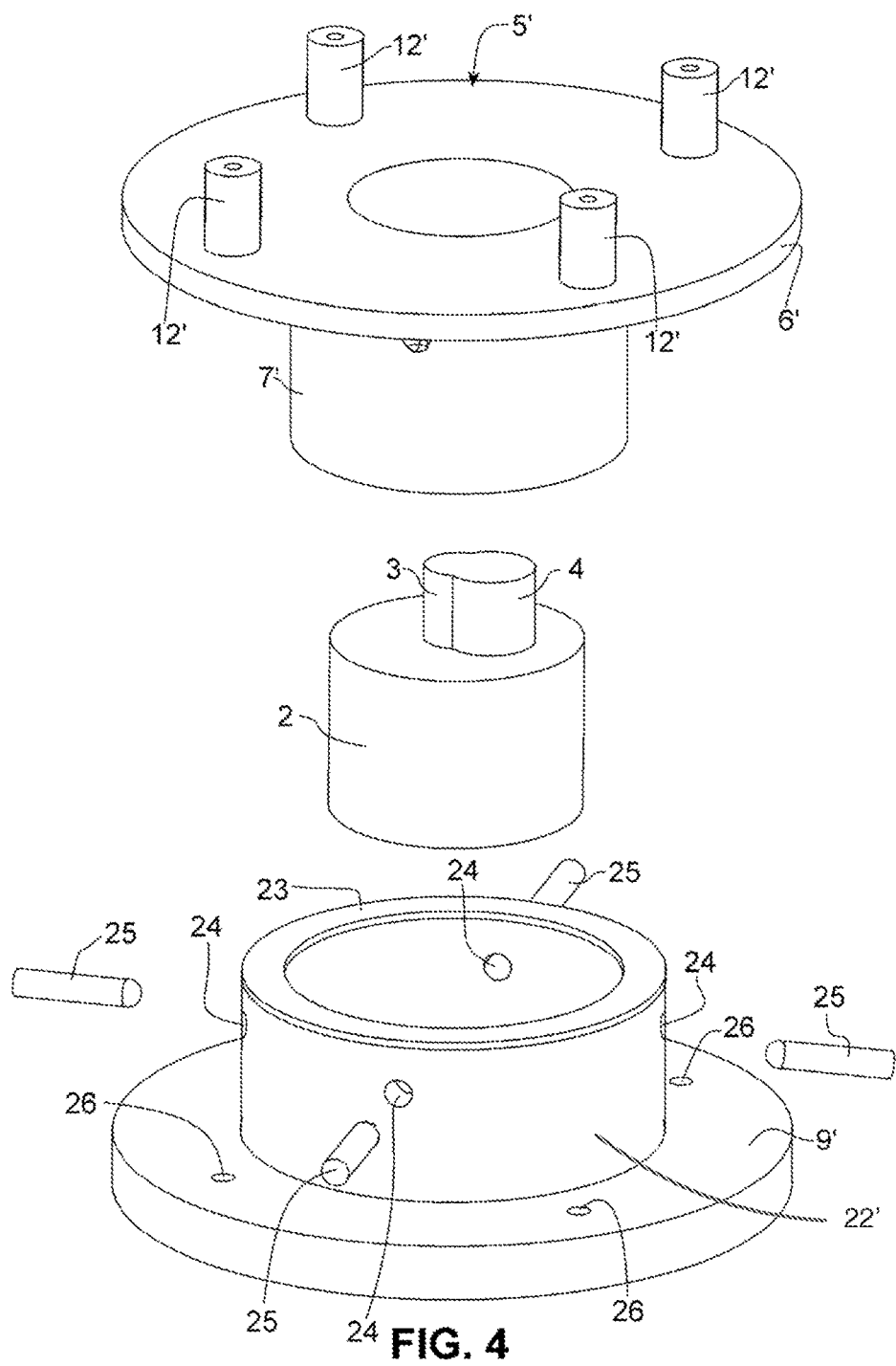
FIG. 4 shows the structural elements of an alternative embodiment of a vibration device.

FIG. 4 shows an exploded view, corresponding to FIG. 3, of the structural elements of an alternative embodiment of the vibration device. Here, the same structural elements are provided with the same reference signs.

Again, there are four connecting elements 12', by means of which a plate 14 having indentations 15 for Petri dishes can be fastened on a vibration body 5' of the vibration device. Said connecting elements 12' are, as shown in FIG. 1, also sealed with respect to the upper wall 19 of the housing 1 via sealing elements 18.

Here too, the electric motor 2 as vibration generator having the imbalance 4 on its motor axis 3 is inserted into an accommodation segment 7' of the vibration body 5'. However, in this case, the vibration body 5' is not connected to the foot 9' by means of springs, but rests on said foot such that it is freely displaceable in any direction. For this purpose, the ring 22' of the foot 9' is configured to be taller and has a greater wall thickness. The upper region of the ring 22' is formed by an annular support 23 composed of a low-friction plastic, for example PTFE (polytetrafluoroethylene). The bottom side of the flange plate 6' of the vibration body 5' rests on this PTFE ring 23. The vibration body 5' is consequently smoothly displaceable with respect to the foot 9' with low friction.

Furthermore, it can be seen in FIG. 4 that the ring 22' of the foot 9' has four threaded holes 24. It is possible to screw four headless screws 25 into said threaded holes 24. By means of the headless screws 25, it is possible to adjust the distance across which the vibration body 5' can freely move. Said distance corresponds to the maximum amplitude of the movement of the vibration body 5' with respect to the foot 9'. Said amplitude is consequently adjustable by means of the headless screws.

The features of the invention that are disclosed in the present description, in the drawings and in the claims can, both individually and in any desired combinations, be essential for the realization of the invention in its various embodiments. The invention is not restricted to the described embodiments. It can be varied within the scope of the claims and in consideration of the knowledge of the responsible person skilled in the art.

The invention claimed is:

1. A vibration device, comprising:
   a housing;
   at least one vibration generator disposed in the housing so that the housing encloses the vibration generator;
   a carrier for at least one Petri dish, the carrier being arranged outside the housing and connected to the vibration generator via at least one connecting element protruding through an opening in a wall of the housing; and
   a sealing element that seals the connecting element with respect to the wall of the housing, wherein the sealing element comprises a flexible silicone seal which fills the opening and is firmly affixed to a surface of the connecting element and to the wall of the housing such that said sealing element permits relative movement between the at least one connecting element and the wall of the housing.

2. The vibration device as claimed in claim 1, wherein the vibration generator and the connecting element are separately fastened to a vibration body disposed inside the housing.

3. The vibration device as claimed in claim 2, wherein the vibration body is supported by a foot disposed inside the housing.

4. The vibration device as claimed in claim 3, wherein a low friction element is arranged between the vibration body and the foot inside the housing.

5. The vibration device as claimed in claim 3, wherein a spring element is arranged between the vibration body and the foot inside the housing.

6. The vibration device as claimed in claim 3, further comprising:
   a screw provided in the foot to adjust amplitude of vibration.

7. The vibration device as claimed in claim 1, further comprising:
   a pressure equalization element, arranged in a wall of the housing, that allows gas molecules to pass through and holds back liquid molecules.

8. The vibration device as claimed in claim 1, wherein the carrier is formed by a plate having indentations that correspond to a diameter of a Petri dish.

9. The vibration device as claimed in claim 1, further comprising:

additional connecting elements protruding through a wall of the housing that connect the carrier to the vibration generator and that are each connected to the carrier by a fastening screw; and additional sealing elements that seal the additional connecting elements with respect to the wall of the housing, wherein each sealing element comprises a flexible silicone seal which fills the opening and is firmly affixed to a surface of the respective additional connecting element and to the wall of the housing.

10. The vibration device as claimed in claim 1, wherein the vibration generator is an electric motor having an imbalance on an axis of the motor.

11. The vibration device as claimed in claim 1, further comprising:
limitation means for limiting an amplitude of vibration.

12. The vibration device as claimed in claim 11, wherein the limitation means is adjustable.

13. The vibration device of claim 1, wherein the flexible silicone seal is formed from a gel-type silicone.

14. A vibration device, comprising:
a housing;
at least one vibration generator disposed in the housing;
a carrier for at least one Petri dish, the carrier being arranged outside the housing and connected to the vibration generator via at least one connecting element protruding through a wall of the housing; and
a sealing element that seals the connecting element with respect to the wall of the housing,
wherein the vibration generator and the connecting element are separately fastened to a vibration body,
wherein the vibration body is supported by a foot, and
wherein a low friction element is arranged between the vibration body and the foot.

15. The vibration device as claimed in claim 14, further comprising:
a pressure equalization element, arranged in a wall of the housing, that allows gas molecules to pass through and holds back liquid molecules.

16. The vibration device as claimed in claim 14, wherein the carrier is formed by a plate having indentations that correspond to a diameter of a Petri dish.

17. The vibration device as claimed in claim 14, further comprising:
additional connecting elements that are each connected to the carrier by a fastening screw.

18. A vibration device, comprising:
a housing;
at least one vibration generator disposed in the housing;
a carrier for at least one Petri dish, the carrier being arranged outside the housing and connected to the vibration generator via at least one connecting element protruding through a wall of the housing; and
a sealing element that seals the connecting element with respect to the wall of the housing,
wherein the vibration generator and the connecting element are separately fastened to a vibration body,
wherein the vibration body is supported by a foot, and
wherein the vibration device further comprises a screw provided in the foot to adjust amplitude of vibration.

19. The vibration device as claimed in claim 18, further comprising:
a pressure equalization element, arranged in a wall of the housing, that allows gas molecules to pass through and holds back liquid molecules.

20. The vibration device as claimed in claim 18, wherein the carrier is formed by a plate having indentations that correspond to a diameter of a Petri dish.

21. The vibration device as claimed in claim 18, further comprising:
additional connecting elements that are each connected to the carrier by a fastening screw.

22. A vibration device, comprising:
a housing;
at least one vibration generator disposed in the housing;
a carrier for at least one Petri dish, the carrier being arranged outside the housing and connected to the vibration generator via at least one connecting element protruding through a wall of the housing; and
a sealing element that seals the connecting element with respect to the wall of the housing,
wherein the vibration generator and the connecting element are separately fastened to a vibration body disposed inside the housing,
wherein the vibration body is supported by a foot disposed inside the housing, and
wherein at least one rubber elastic spring element is arranged between the vibration body and the foot inside the housing.

23. The vibration device as claimed in claim 22, further comprising:
a pressure equalization element, arranged in a wall of the housing, that allows gas molecules to pass through and holds back liquid molecules.

24. The vibration device as claimed in claim 22, wherein the carrier is formed by a plate having indentations that correspond to a diameter of a Petri dish.

25. The vibration device as claimed in claim 22, further comprising:
additional connecting elements that are each connected to the carrier by a fastening screw.

* * * * *